(12) United States Patent
Dewey et al.

(10) Patent No.: US 9,846,114 B2
(45) Date of Patent: Dec. 19, 2017

(54) TRANSMISSOMETER MANIFOLD

(71) Applicant: WET Labs, Inc., Philomath, OR (US)

(72) Inventors: Michael Dewey, Philomath, OR (US); Corey Koch, Philomath, OR (US)

(73) Assignee: WET Labs, Inc., Philomath, OR (US)

( * ) Notice: Subject to any disclaimer, the term of this patent is extended or adjusted under 35 U.S.C. 154(b) by 0 days.

(21) Appl. No.: 15/064,766

(22) Filed: Mar. 9, 2016

(65) Prior Publication Data

US 2017/0261422 A1    Sep. 14, 2017

(51) Int. Cl.
  *G01N 21/00* (2006.01)
  *G01N 21/05* (2006.01)
  *G01N 21/59* (2006.01)

(52) U.S. Cl.
  CPC ............ *G01N 21/05* (2013.01); *G01N 21/59* (2013.01); *G01N 2021/054* (2013.01)

(58) Field of Classification Search
  CPC ... G01N 21/05; G01N 21/59; G01N 2021/054
  USPC .................................................. 356/432–444
  See application file for complete search history.

(56) References Cited

U.S. PATENT DOCUMENTS 5,134,079 A * 7/1992 Cusack ................. G01N 35/08
422/81

* cited by examiner

*Primary Examiner* — Tri T Ton
(74) *Attorney, Agent, or Firm* — Perkins Coie LLP

(57) ABSTRACT

Technology is provided for a fluid transmissometer manifold. The transmissometer manifold includes a manifold body having an upwardly extending bubble diverter passageway with an upper end portion and a lower end portion. A flow restrictor is connected to the upper end portion and an inlet passageway is connected to the diverter passageway between the flow restrictor and the lower end portion. An upwardly extending optical chamber is connected to the lower end portion. At least a portion of a fluid entering the inlet passageway flows downward into the optical chamber and any bubbles contained in the fluid travel upward through the bubble diverter passageway. A light source can be positioned at a first end of the optical chamber and a detector positioned at a second end of the optical chamber opposite the light source and operative to detect light emitted from the light source.

21 Claims, 4 Drawing Sheets

TRANSMISSOMETER MANIFOLD

TECHNICAL FIELD

This patent application is directed to fluid property measurement and, more specifically, to a transmissometer manifold.

BACKGROUND

A fluid transmissometer measures the fraction of light, emitted from a light source, traveling through a fluid (e.g., water), and reaching a light detector a set distance away. Light which is absorbed or scattered by the fluid positioned between the source and the detector does not reach the detector. Therefore, the fraction of light received by the light detector is indicative of the composition of the fluid.

BRIEF DESCRIPTION OF THE DRAWINGS

Embodiments of the transmissometer manifold introduced herein may be better understood by referring to the following Detailed Description in conjunction with the accompanying drawings, in which like reference numerals indicate identical or functionally similar elements.

Figure 1:
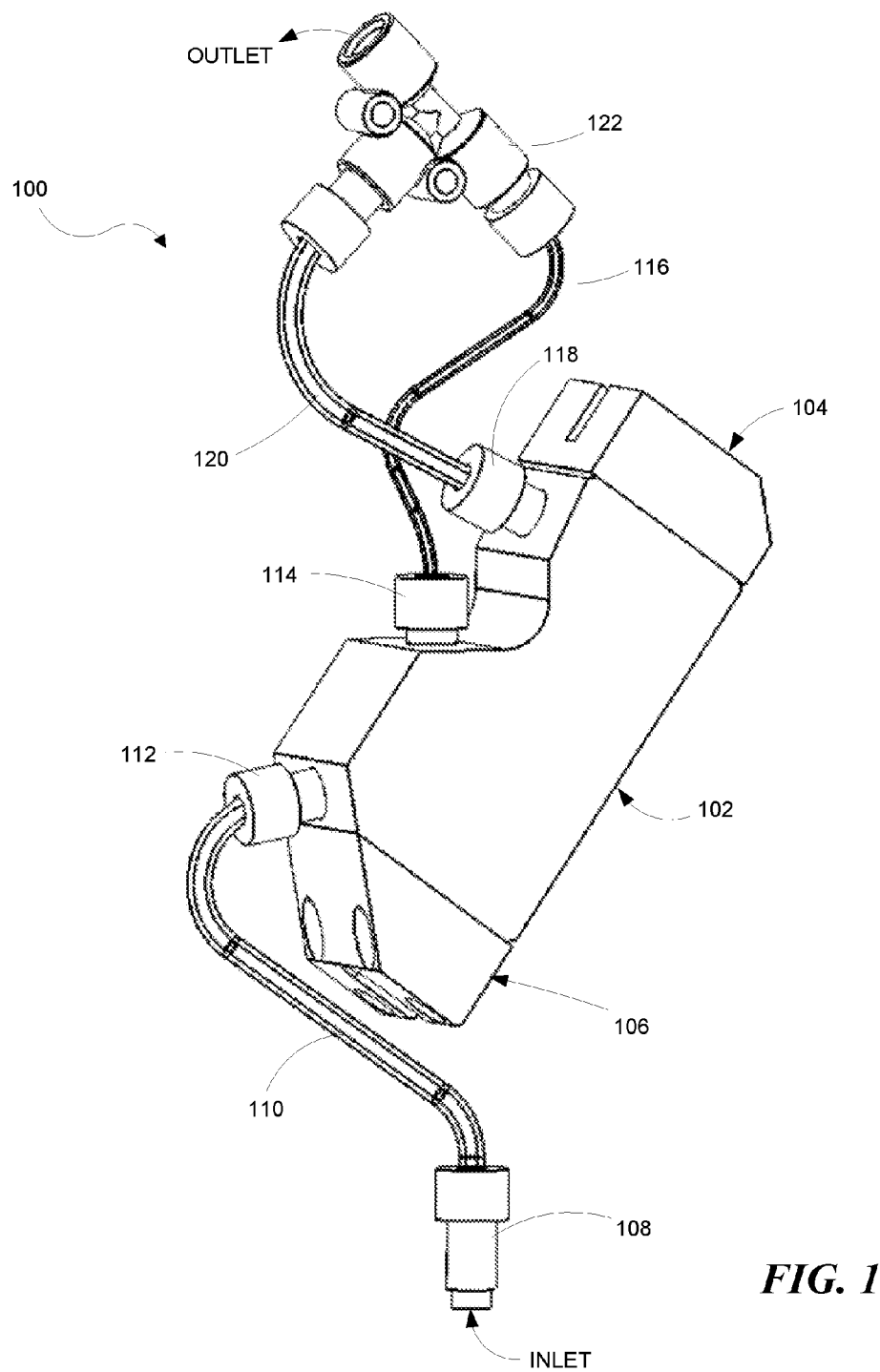
FIG. 1 is an isometric view of a transmissometer according to a representative embodiment.

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Moreover, while the disclosed technology is amenable to various modifications and alternative forms, specific embodiments have been shown by way of example in the drawings and are described in detail below. The intention, however, is not to limit the embodiments described. On the contrary, the embodiments are intended to cover all modifications, equivalents, and alternatives falling within the scope of the embodiments as defined by the appended claims.

DETAILED DESCRIPTION

Overview

A fluid transmissometer manifold is disclosed. The disclosed transmissometer manifold design helps prevent bubbles and buoyant debris entrained in a fluid sample from entering the optical chamber of a transmissometer and interfering with measurements of the fluid. In an embodiment, the fluid transmissometer includes a manifold body having an upwardly extending bubble diverter passageway with an upper end portion and a lower end portion. A flow restrictor is connected to the upper end portion and an inlet passageway is connected to the diverter passageway between the flow restrictor and the lower end portion. An upwardly extending optical chamber is connected to the lower end portion. At least a portion of a fluid entering the inlet passageway flows downward into the optical chamber and any bubbles contained in the fluid travel upward through the bubble diverter passageway. The outlet of the optical chamber is connected to the outlet of the bubble diverter passageway so that bubbles are recombined with the post-measurement sample into a singular system outlet. In some embodiments, a light source is positioned at a first end of the optical chamber and a detector is positioned at a second end of the optical chamber opposite the light source and operative to detect light emitted from the light source.

General Description

Various examples of the device and systems introduced above will now be described in further detail. The following description provides specific details for a thorough understanding and enabling description of these examples. One skilled in the relevant art will understand, however, that the techniques discussed herein may be practiced without many of these details. Likewise, one skilled in the relevant art will also understand that the technology can include many other features not described in detail herein. Additionally, some well-known structures or functions may not be shown or described in detail below so as to avoid unnecessarily obscuring the relevant description.

The terminology used below is to be interpreted in its broadest reasonable manner, even though it is being used in conjunction with a detailed description of some specific examples of the embodiments. Indeed, some terms may even be emphasized below; however, any terminology intended to be interpreted in any restricted manner will be overtly and specifically defined as such in this section.

As shown in FIG. 1, the transmissometer 100 includes a transmissometer manifold 102, a light detector endcap 104, and a light source endcap 106. A fluid sample to be measured flows into inlet fitting 108 through inlet tubing 110 and into the transmissometer manifold 102 via inlet port fitting 112. As explained more fully below with respect to FIG. 2, bubbles and other buoyant debris are separated from the fluid sample prior to being measured. Bubbles and debris separated from the fluid sample exit the manifold 102 via diverter port fitting 114 and through diverter tubing 116. The measured sample exits manifold 102 via outlet port fitting 118 and outlet tubing 120. The measured sample and bubbles are recombined in outlet tee union or fitting 122. Thus, the tee fitting provides a single outlet for the measured sample. In some embodiments, the inlet tubing 110 and outlet tubing 120 are comprised of ⅛ inch tubing having a 1/16 inch inner diameter. In some embodiments, the diverter passageway tubing is 1/16 inch tubing having a 0.030 inch inner diameter. In some embodiments, the outlet tee fitting 122 has a through path with a 3/32 inch inner diameter and a perpendicular path of 0.0625 inches in diameter.

Figure 2:
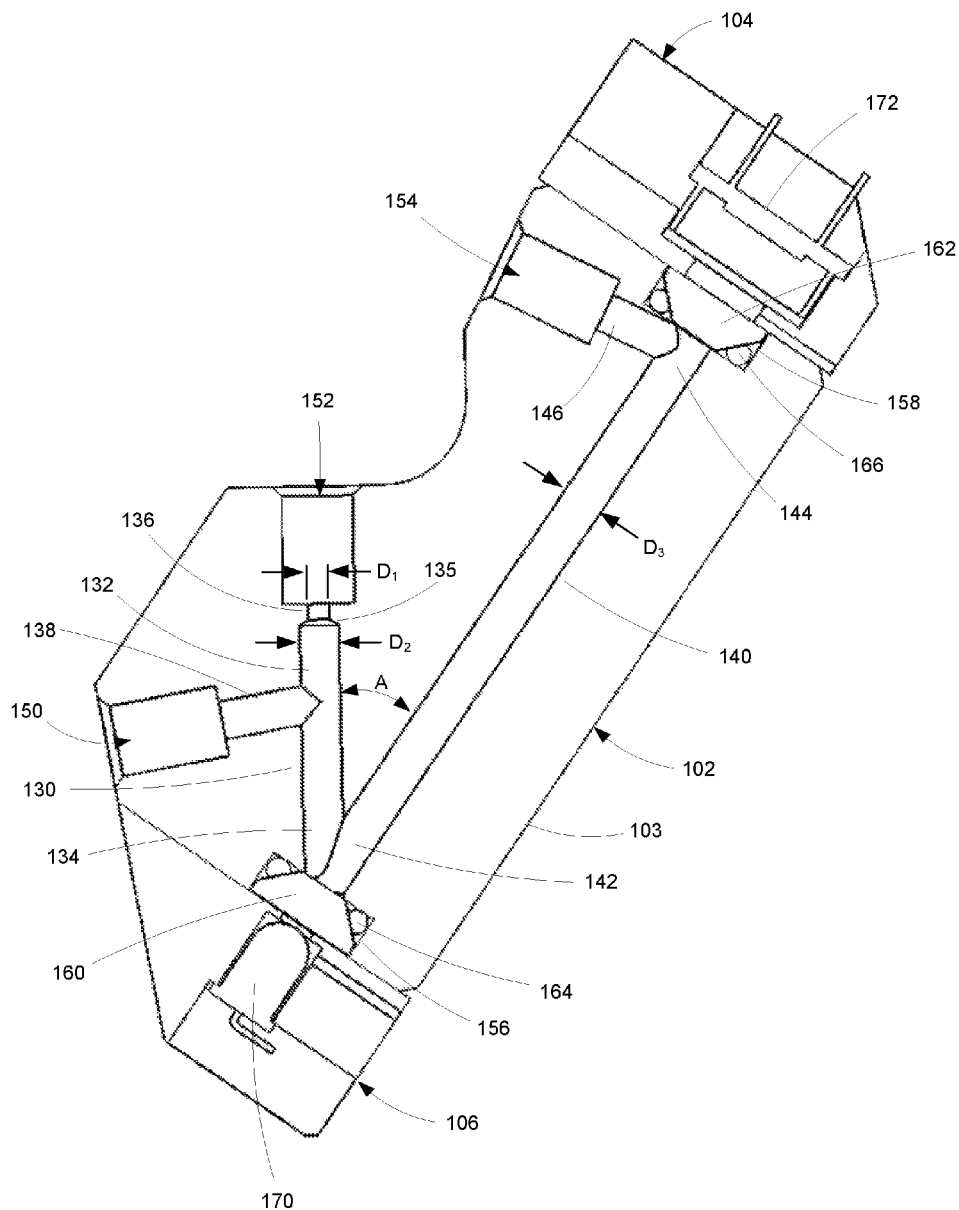
FIG. 2 is a side view in cross-section of the transmissometer shown in FIG. 1 with various components removed for clarity.

With reference to FIG. 2, the transmissometer manifold 102 comprises a manifold body 103 including an upwardly extending bubble diverter passageway 130 (e.g., a first passageway) having an upper end portion 132 and a lower end portion 134. A flow restrictor 136 is connected to the upper end portion 132. An inlet passageway 138 (e.g., a second passageway) is connected to the diverter passageway 130 between the flow restrictor 136 and the lower end portion 134. An upwardly extending optical chamber 140 (e.g., third passageway and/or measurement chamber) is connected to the lower end portion 134 of the diverter passageway 130. The upper end portion 132 includes a partial drill point 135 intersecting with the flow restrictor 136 (e.g., a fourth passageway). The resulting chamfered corner or transition facilitates movement of bubbles out of the upper end portion 132 of the diverter passageway 130.

The diameter $D_1$ of the flow restrictor 136, the diameter $D_2$ of the diverter passageway 130, and the diameter $D_3$ of the optical chamber 140 are sized relative to each other to cause the majority of the fluid sample entering the inlet passageway 138 to flow through the lower end portion 134 and into the optical chamber 140, while allowing bubbles and buoyant debris to pass through the flow restrictor 136 and out of the manifold body 103. In at least one embodiment, the bubble diverter passageway has an inner diameter $D_2$ of approximately 0.116 inches and the flow restrictor has an inner diameter $D_1$ of approximately 0.030 inches. In at least one embodiment, the inner diameter $D_3$ of optical chamber 140 is approximately 0.125 inches. In some embodiments, the diameter $D_3$ of the optical chamber 140 is approximately the same diameter $D_2$ as the bubble diverter passageway 130. In addition to the diameters ($D_1$, $D_2$, and $D_3$) being sized to control the proportion of fluid diverted around the optical chamber 140, the lengths of the outlet tubing 120 and diverter tubing 116 (see FIG. 1) are also sized. In an embodiment, the outlet tubing 120 is 2.85 inches long with an inner diameter of 1/16" and the diverter tubing 116 is 4.48 inches long with an inner diameter of 0.030 inches.

The fluid enters the inlet passageway 138 through inlet port 150. The portion of fluid containing the bubbles that flows upward through the upper end portion 132 exits the manifold body 103 through an outlet port 152. The optical chamber 140 includes an inlet end 142 connected to the lower end portion 134 and also includes an outlet end 144 connected to an outlet passageway 146. Fluid traveling through the optical chamber 140 exits the manifold body 103 via the outlet passageway 146 and the outlet port 154 connected to passageway 146. In some embodiments, the ports 150, 152, and 154 comprise threaded bores sized and configured to receive appropriate fittings, such as fittings 112, 114, and 118 (see FIG. 1).

With continued reference to FIG. 2, it can be appreciated that the bubble diverter passageway 130 is substantially vertically oriented. Preferably, the diverter passageway 130 is positioned vertically within approximately ±15° from vertical. The vertical orientation of the bubble diverter passageway 130 is preferable in that it provides maximum buoyant force to remove the bubbles from the flow path. It should also be appreciated that, in general, the passageways of the manifold body 103 are upwardly extending passageways to help prevent bubbles from being trapped within the transmissometer. The bubble diverter passageway 130 and the optical chamber 140 are oriented at an angle A with respect to each other. In one embodiment, angle A is approximately 35°.

Inlet end 142 of the optical chamber 140 intersects a lower window bore 156 at one end of the manifold body 103. Similarly, the outlet end 144 of the optical chamber 140 intersects an upper window bore 158. The window bores 156 and 158 are sized and configured to receive optical windows 160 and 162, respectively. Each optical window 160 and 162 is sealed in the window bores 156 and 158 with O-rings 166 and 164, respectively.

Figure 3:
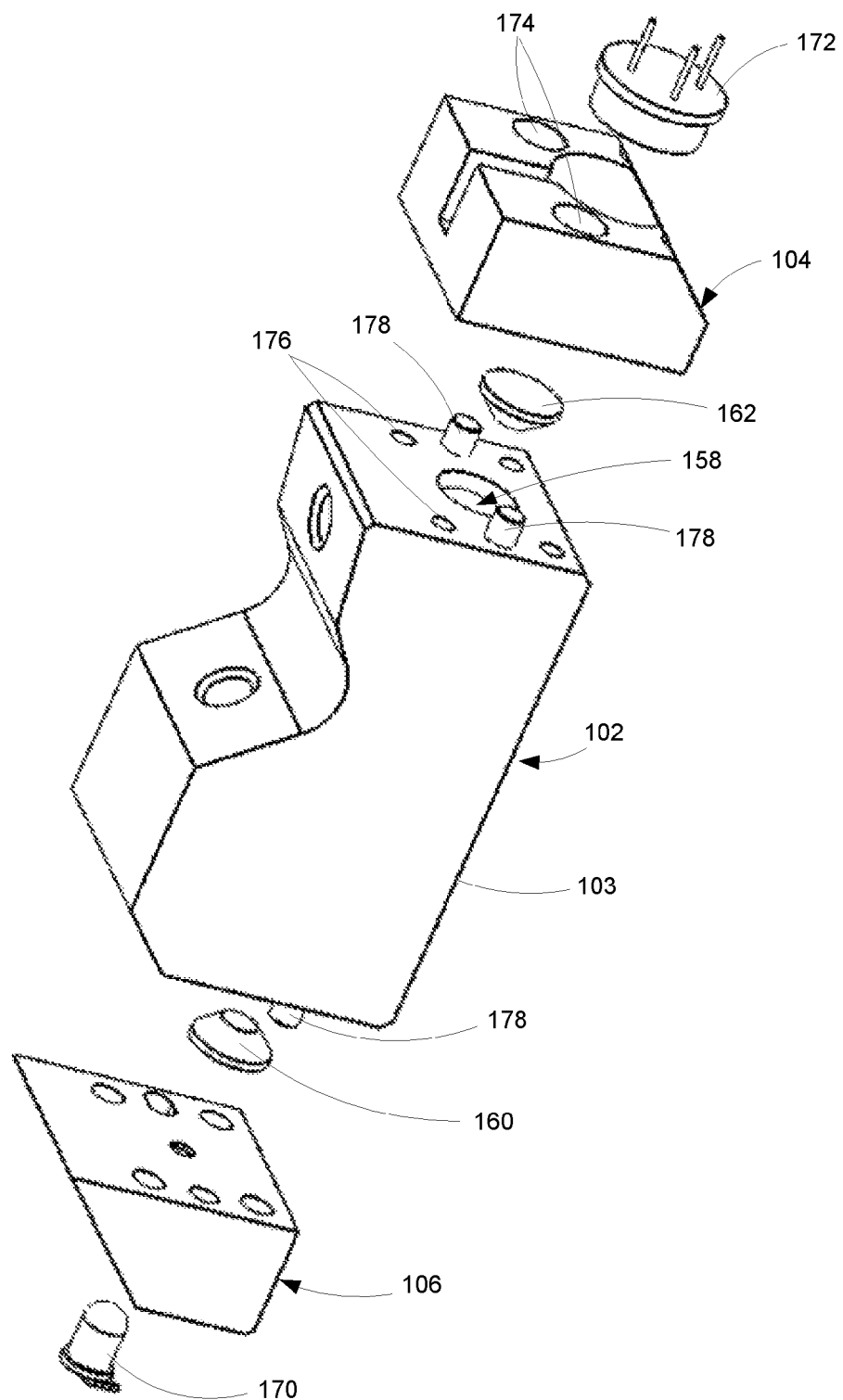
FIG. 3 is an exploded isometric view of the transmissometer shown in FIGS. 1 and 2.

With further reference to FIG. 3, the optical windows 160 and 162 are retained in their respective window bores 156 and 158 by the endcaps 104 and 106. The endcap 104 houses the light detector 172, which receives light through the optical chamber 140 from the light source 170, which is housed in endcap 106. Endcaps 104 and 106 are mounted to the manifold body 103 with suitable fasteners (not shown) that extend through clearance holes 174 and engage into threaded holes 176 located on the manifold body 103. In some embodiments, the manifold body 102 may include locating pins 178, which correspondingly mate with apertures on the endcaps 104 and 106. Optical windows 160 and 162 seal the ends of the optical chamber 140 and provide transparent windows through which the light source 170 and detector 172 can operate to detect properties of the fluid contained in the fluid chamber 140. The manifold body 103 and endcaps 104 and 106 can be comprised of any suitable material such as metal or plastic. In various embodiments, the manifold body and endcaps can be comprised of titanium, steel, aluminum, acetal resin, polyethylene, or combinations thereof, for example. In some embodiments, the optical windows 160 and 162 are comprised of glass or other suitable transparent material such as optical plastics including, for example, polycarbonate, acrylic, polystyrene, and the like.

Although the passageways in the manifold body 103 have been described as having particular angles, orientations, and dimensions, other angles, orientations, and dimensions may be used without departing from the disclosed technology.

Figure 4:
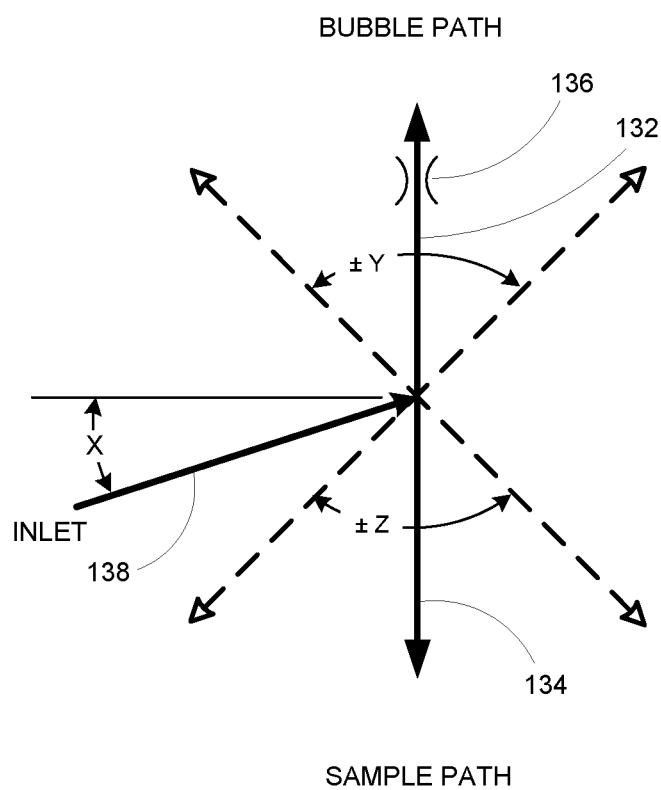
FIG. 4 is a schematic representation of selected transmissometer manifold fluid passageways.

For example, as shown in FIG. 4, the inlet passageway 138 can be angled with respect to horizontal by an angle X. In some embodiments, angle X can range from 0-90 degrees. In at least one embodiment, angle X is less than approximately 30 degrees from horizontal so that bubbles are separated to the top of the inlet passageway 138 and guided to the upper end portion 132. The upper end portion 132 of the diverter passageway 130 can be angled with respect to vertical at an angle of ±Y degrees. In one embodiment, Y is approximately ±45 degrees. The lower end portion 134 can vary from vertical by an angle of ±Z degrees. In one embodiment, Z is approximately ±45 degrees.

Remarks

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. It will be appreciated that the same thing can be said in more than one way. Consequently, alternative language and synonyms may be used for any one or more of the terms discussed herein, and any special significance is not to be placed upon whether or not a term is elaborated or discussed herein. Synonyms for some terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification. Unless otherwise defined, all technical and scientific terms used herein have the same meaning as commonly understood by one of ordinary skill in the art to which this disclosure pertains. In the case of conflict, the present document, including definitions, will control.

What is claimed is:

1. A fluid measurement manifold, comprising:
a manifold body, including:
an upwardly extending first passageway having an upper end portion and a lower end portion;
a flow restrictor connected to the upper end portion;
a second passageway connected to the first passageway between the flow restrictor and the lower end portion; and
an upwardly extending measurement chamber connected to the lower end portion;
wherein at least a portion of a fluid entering the second passageway flows downward into the measurement chamber and any bubbles contained in the fluid travel upward through the first passageway.

2. The fluid measurement manifold of claim 1, wherein the flow restrictor comprises an orifice.

3. The fluid measurement manifold of claim 1, wherein the flow restrictor comprises a fourth passageway formed in the manifold body having a diameter smaller than a diameter of the upper end portion.

4. The fluid measurement manifold of claim 1, wherein the flow restrictor comprises a length of tubing having an inner diameter smaller than a diameter of the upper end portion.

5. The fluid measurement manifold of claim 1, wherein the measurement chamber has an inlet end connected to the lower end portion and an outlet end, and further comprising an outlet passageway connected to the outlet end.

6. The fluid measurement manifold of claim 5, wherein the outlet passageway and the flow restrictor are connected to provide a single outlet.

7. A fluid transmissometer manifold, comprising:
a manifold body, including:
an upwardly extending bubble diverter passageway having an upper end portion and a lower end portion;
a flow restrictor connected to the upper end portion;
an inlet passageway connected to the diverter passageway between the flow restrictor and the lower end portion; and
an upwardly extending optical chamber connected to the lower end portion;
wherein at least a portion of a fluid entering the inlet passageway flows downward into the optical chamber and any bubbles contained in the fluid travel upward through the bubble diverter passageway.

8. The fluid transmissometer manifold of claim 7, wherein the optical chamber has an inlet end connected to the lower end portion and an outlet end, further comprising an outlet passageway connected to the outlet end.

9. The fluid transmissometer manifold of claim 8, wherein the outlet passageway and the flow restrictor are connected.

10. The fluid transmissometer manifold of claim 9, further comprising a tee union interconnecting the outlet passageway and the flow restrictor, wherein the tee union has a singular outlet.

11. The fluid transmissometer manifold of claim 7, wherein the bubble diverter passageway has an inner diameter of approximately 0.116 inches and the flow restrictor has an inner diameter of approximately 0.030 inches.

12. The fluid transmissometer manifold of claim 7, wherein the bubble diverter passageway and the optical chamber are oriented at an angle of approximately 35 degrees with respect to each other.

13. The fluid transmissometer manifold of claim 7, wherein the bubble diverter passageway is substantially vertically oriented.

14. A fluid transmissometer, comprising:
a manifold body, including:
an upwardly extending bubble diverter passageway having an upper end portion and a lower end portion;
a flow restrictor connected to the upper end portion;
an inlet passageway connected to the diverter passageway between the flow restrictor and the lower end portion; and
an upwardly extending optical chamber connected to the lower end portion;
wherein at least a portion of a fluid entering the inlet passageway flows downward into the optical chamber and any bubbles contained in the fluid travel upward through the bubble diverter passageway;
a light source positioned at a first end of the optical chamber; and
a detector positioned at a second end of the optical chamber opposite the light source and operative to detect light emitted from the light source.

15. The fluid transmissometer of claim 14, wherein the first end of the optical chamber is connected to the lower end portion, and further comprising an outlet passageway connected to the second end of the optical chamber.

16. The fluid transmissometer of claim 15, wherein the flow restrictor comprises a length of tubing having an inner diameter smaller than a diameter of the upper end portion.

17. The fluid transmissometer of claim 16, wherein the outlet passageway and the flow restrictor are connected.

18. The fluid transmissometer of claim 17, further comprising a tee union interconnecting the outlet passageway and the flow restrictor, wherein the tee union has a singular outlet.

19. The fluid transmissometer of claim 14, wherein the bubble diverter passageway has an inner diameter of approximately 0.116 inches and the flow restrictor has an inner diameter of approximately 0.030 inches.

20. The fluid transmissometer of claim 14, wherein the bubble diverter passageway and the optical chamber are oriented at an angle of approximately 35 degrees with respect to each other.

21. The fluid transmissometer of claim 14, wherein the bubble diverter passageway is substantially vertically oriented.

* * * * *